(12) United States Patent
Abbas et al.

(10) Patent No.: US 7,361,499 B1
(45) Date of Patent: Apr. 22, 2008

(54) **NON-AFLATOXIGENIC *ASPERGILLUS FLAVUS* ISOLATES**

(75) Inventors: Hamed K. Abbas, Greenville, MS (US); Robert M. Zablotowicz, Cleveland, MS (US)

(73) Assignee: The United States of America, as represented by the Secretary of Agriculute, Washington, DC (US)

( * ) Notice: Subject to any disclaimer, the term of this patent is extended or adjusted under 35 U.S.C. 154(b) by 257 days.

(21) Appl. No.: 11/033,352

(22) Filed: Jan. 11, 2005

(51) Int. Cl.
*C12P 1/00* (2006.01)
*A01N 63/04* (2006.01)
(52) U.S. Cl. .................. 435/256.1; 424/93.5
(58) Field of Classification Search ............ None
See application file for complete search history.

(56) References Cited

U.S. PATENT DOCUMENTS 5,171,686 A * 12/1992 Cotty ............... 435/256.1
6,306,386 B1 * 10/2001 Cole et al. ............ 424/93.5

* cited by examiner

*Primary Examiner*—Irene Marx
(74) *Attorney, Agent, or Firm*—John Fado; Evelyn Rabin

(57) ABSTRACT

The ability of two *Aspergillus flavus* Link isolates (CT3 and K49) to reduce aflatoxin contamination of corn was assessed in a four-year field study (2001 to 2004). Soil was treated with six wheat inoculant treatments: toxigenic isolate F3W4; the non-toxigenic isolate K49; the non-aflatoxigenic isolate CT3, two mixtures of CT3 or K49 with F3W4; and an autoclaved wheat control, applied at 20 kg/ha. In 2001, inoculation with the toxigenic isolate increased corn grain aflatoxin levels by 167% compared to the non-inoculated control, while CT3 and K49 inoculation reduced aflatoxin levels in corn grain by 86% & 60%, respectively. In 2002, inoculation of CT3 and K49 reduced aflatoxin levels by 61% and 76% compared to non-inoculated controls, respectively. In 2001 mixtures of toxigenic and non-toxigenic isolates had little effect on aflatoxin levels, but in 2002 inoculation with mixtures of K49 and CT3 reduced aflatoxin levels 68 and 37% compared to non-inoculated controls, respectively. In 2003 and 2004, a low level of natural aflatoxin contamination was observed (8 ng/g). However, inoculation with mixtures of K49+F3W4 and CT3+F3W4, reduced levels of aflatoxin 65 to 94% compared to the toxigenic strain alone. Compared to the non-sclerotia producing CT3, strain K49 produces large sclerotia, has more rapid in vitro radial growth, and a greater ability to colonize corn when artificially inoculated, perhaps indicating greater ecological competence. Results indicate that non-toxigenic, indigenous *A. flavus* isolates, such as strain K49, have potential use for biocontrol of aflatoxin contamination in southern U.S. corn.

4 Claims, 1 Drawing Sheet

NON-AFLATOXIGENIC *ASPERGILLUS FLAVUS* ISOLATES

BACKGROUND OF THE INVENTION

1. Field of the Invention

This invention relates to biocontrol agents for the prevention of aflatoxin contamination in corn, in particular, to certain non-toxicigenic and non-aflatoxigenic *Aspergillus flavus* strains capable of inhibiting growth of fungi which produce aflatoxin, and which are further capable of suppressing production of aflatoxin by the toxigenic fungi. More specifically, the invention relates to the non-toxicigenic *Aspergillus flavus* strain K49 (NRRL 30797) and the non-aflatoxigenic *Aspergillus flavus* strain CT3 (NRRL 30798) and their variants. The present invention relates to a biocontrol strategy whereby the *A. flavus* strains K49 and CT3 are applied to crops as a method for reducing aflatoxin contamination in corn, particularly in the Mississippi Delta.

2. Description of the Relevant Art

Aflatoxins are a class of mycotoxins produced by *Aspergillus flavus* Link and *A. parasiticus* Speare. There are four closely related aflatoxins: B1, B2, G1, and G2 (Council for Agricultural Science and Technology [CAST]. 2003. *Task Force Report* 139, Ames, Iowa; Diener et al. 1987. *Ann. Rev. Phytopath.* 25: 249-270). Toxigenic strains of *A. flavus* produce mainly B1 and B2, while *A. parasiticus* produces all four aflatoxins (CAST, 2003; Diener et al., supra). Aflatoxins are potent carcinogens and hepatotoxins. Aflatoxin contamination of corn (maize, *Zea mays* L.) is a significant problem worldwide (CAST, supra; Cullen et al. 1994. In: *The Toxicology of Aflatoxins*, Eaton et al. (Eds.), Academic Press, San Diego, Calif., pp. 3-26). United States federal guidelines for food and feed set a limit of 20 ng/g total aflatoxins, while the European Union guidelines are more strict, with a limit of 1 ng/g limit for B1 and a 4 ng/g limit for total aflatoxins (van Egmond, H. P. & Jonker, M. A. 2004. *J. Toxicol.-Toxin Rev.* 23: 273-293).

Cyclopiazonic acid (CPA) is another mycotoxin also produced by various *Aspergillus* species that may cause toxicological problems in animals (Bryden, W. L. 1991. In: *Emerging Problems Resulting from Microbial Contamination*, Mixe et al. (Eds.), National Institute of Hygienic Science, Tokyo, pp. 127-147). Cyclopiazonic acid has been found to occur in maize and other foods (Trucksess et al. 1987. *J. Assoc. Official Analytical Chem. Int'l.* 70: 123-126) and can further increase the risks of food and feed contaminated with *A. flavus* (Takahashi et al. 2004. *J. Food Protect.* 67: 90-95; Mphande et al. 2004. *J. Food Protect.* 67: 96-102; Sosa et al. 2002. *J. Food Protect.* 65: 988-992). Residues of CPA from feed can be transferred into milk and eggs (Dorner et al. 1983. *Appl. Environ. Microbiol.* 46: 698-703; CAST, supra). Strains of *A. flavus* vary greatly in aflatoxin production, with some producing copious amounts and others none (Abbas et al. 2004. *J. Toxicol.-Toxin Rev.* 23 (2,3): 153-450; Horn, B. W. 2003. *J. Toxicol.-Toxin Rev.* 22: 351-379). Many *A. flavus* strains produce both CPA and aflatoxins whereas other strains are non-toxicigenic, i.e., the strains produce neither aflatoxins nor CPA. Other strains are non-aflatoxigenic, that is, they produce CPA, but do not produce aflatoxin (Horn and Dorner. 1999. *Appl. Environ. Microbiol.* 65: 1444-1449; Dorner, J. W. 2004. *J. Toxicol.-Toxin Rev.* 23: 425-450; Geiser et al. 2000. *Fungal Genet. Biol.* 31: 169-179).

Because aflatoxin contamination is a major economic and food safety concern, strategies have been developed to control aflatoxin in crops (Abbas, H. K. 2003. *J. Toxicol.-Toxin Rev.* 22 (2,3): 139-459; Abbas, H. K., 2004, supra; 2002. Aflatoxin/Fumonisin Elimination and Fungal Genomics Workshops, Phoenix, Ariz., Oct. 23-26, 2001, Robens, J. F. & Riley, R. T. (Eds.) *Mycopathologia* 155: 1-122; 2004. Aflatoxin/Fumonisin Elimination and Fungal Genomics Workshops, San Antonio, Tex., Oct. 23-26, 2002, Robens, J. F. & Brown, R. L. (Eds.) *Mycopathologia* 157: 393-505). Non-toxic strains of *A. flavus* have been suggested as biological control agents in hopes that they might compete with naturally-occurring toxigenic *A. flavus*. Early in vitro studies by Erhlich (Erhlich, K. 1987. *Mycopathologia* 97: 93-96) showed that co-inoculation of medium with a mixture of non-toxic mutants and the toxigenic wild-type significantly reduced aflatoxin contamination. The potential for biological control of aflatoxin has been demonstrated under field conditions in cotton (*Gossypium hirsutum* L.) and peanut (*Arachis hypogaea* L.). Cotty has shown that a non-toxic strain of *A. flavus* and a factor produced by a non-toxic strain of *A. flavus* can reduce aflatoxin contamination in cotton (Cotty, P. J. 1994a. *Phytopath.* 84: 1270-1277; Cotty, P. J. 1994b. U.S. Pat. No. 5,294,442, Mar. 15 1994; Cotty, P. J., U.S. Pat. No. 5,171,686, Dec. 15 1992). Others have utilized either a mixture of the non-toxic strains of *A. parasiticus* and *A. flavus*, oil formulations of these strains, or other *Aspergillus* strains: *A. oryzae*, *A. sojae*, and mixtures of *A. oryzae* and *A. sojae*, to reduce aflatoxin contamination in peanut (Cole et al. U.S. Pat. No. 5,292,661, Mar. 8 1994; Cole et al. U.S. Pat. No. 6,306,386, Oct. 23 2001; Dorner, J. W. and Cole, R. J. 2002. *J. Stored Prod. Res.* 38: 329-339; Dorner et al. U.S. Pat. No. 6,027,724, Feb. 22 2000).

Corn too is frequently infected by *Aspergillus* species which can result in significant aflatoxin accumulation, especially when heat and drought stress occur (Abbas et al. 2002. *J. Agric. Food Chem.* 50: 5246-5254; Payne, G. S. 1992. *Crit. Rev. Plant Sci.* 10: 423-440). When aflatoxin concentration exceeds regulatory levels, this contamination causes a severe economic impact on growers, the grain industry, and may be a significant health risk (Robens, J. & Cardwell, K. 2003. *J. Toxicol.-Toxin Rev.* 22: 139-152). Thus, suitable strategies to control aflatoxin contamination of corn have been sought to reduce the risks in corn production in certain geographical regions, such as the southern United States. In one study by Brown et al., individual ears of corn were wounded and inoculated directly and simultaneously with a spore solution containing toxigenic and atoxigenic *A. flavus* (1991. *J. Food Protect.* 54: 623-626). Brown et al. concluded that atoxigenic strains of *A. flavus* may have potential use as biological control agents to reduce aflatoxin contamination by toxigenic strains. Later studies by Dorner et al. (1999. *J. Food Protect.* 62: 650-656) evaluated the effect of crop rotation and inoculation of corn fields with rice infected with non-aflatoxigenic strains of *A. flavus* and *A. parasiticus* to determine the effect of application of the non-toxicigenic strains on preharvest aflatoxin contamination of corn. Dorner et al. concluded that their study did not indicate that their biocontrol strategy offered a solution to the problem of aflatoxin contamination in corn (Page 655, last paragraph) and that inclusion of a non-aflatoxigenic strain of *A. parasiticus* in a biological control formulation for aflatoxin contamination may not be as important for airborne crops, such as corn, as for soilborne crops, such as peanuts (Page 650, Abstract).

In a survey of *A. flavus* from the Mississippi Delta region of the USA, we characterized over five hundred isolates of *A. flavus* from soil and various crops including corn, rice and peanuts (Abbas et al. 2004. *Canad. J. Microbiol.* 50: 193-

199). Of these isolates, about 36% produced less than 20 ng/g total aflatoxins when grown on potato dextrose agar (PDA). As discussed above, field studies in cotton and peanuts have shown that non-toxigenic strains applied to soil are capable of competing and displacing naturally occurring toxigenic strains (Cotty, P. J., 1992, 1994a and 1994b, supra; Dorner, J. W. & Cole, R. J., 2002, supra; Dorner et al. U.S. 2000, supra; Cole et al., supra). While these various biocontrol methods and formulations for effective control of toxigenic fungi in cotton and peanuts are known in the art, there still remains a need for effective non-aflatoxigenic and non-toxigenic *A. flavus* strains to serve as biocontrol agents for controlling toxigenic *A. flavus* in corn. The present invention, described below, provides non-aflatoxigenic and non-toxigenic *A. flavus* strains and methods of using these strains to effectively reduce aflatoxin contamination in corn.

SUMMARY OF THE INVENTION

We have isolated the non-toxigenic *A. flavus* strain K49 and the non-aflatoxigenic *A. flavus* strain CT3, and discovered that these *A. flavus* strains can reduce aflatoxin contamination, particularly in the Mississippi Delta.

In accordance with this discovery, it is an object of the invention to provide isolated non-aflatoxigenic and non-toxigenic *A. flavus* strains which can act as biocontrol agents and inhibit the proliferation of aflatoxin-producing fungi. In the preferred embodiments of the invention, the non-toxigenic strain designated as K49, the non-aflatoxigenic strain designated as CT3, and variants thereof are provided.

It is a further object of the invention to provide a biocontrol composition for preventing or reducing aflatoxin contamination of corn crops wherein said composition comprises the non-toxigenic *A. flavus* strain K49 or the non-aflatoxigenic strain CT3 as biocontrol agents.

It is another object of the invention to provide a method for biocontrol of toxin-producing fungi in plants.

It is an additional object of the invention to provide a biocontrol method of preventing or reducing aflatoxin contamination of corn which includes applying the non-toxigenic *A. flavus* strain K49 or the non-aflatoxigenic strain CT3 to the soil as biocontrol agents to control aflatoxin.

Also part of this invention is a kit, comprising a biocontrol composition for application to corn crops to prevent or reduce aflatoxin contamination.

Other objects and advantages of this invention will become readily apparent from the ensuing description.

DETAILED DESCRIPTION OF THE INVENTION

Figure 1:
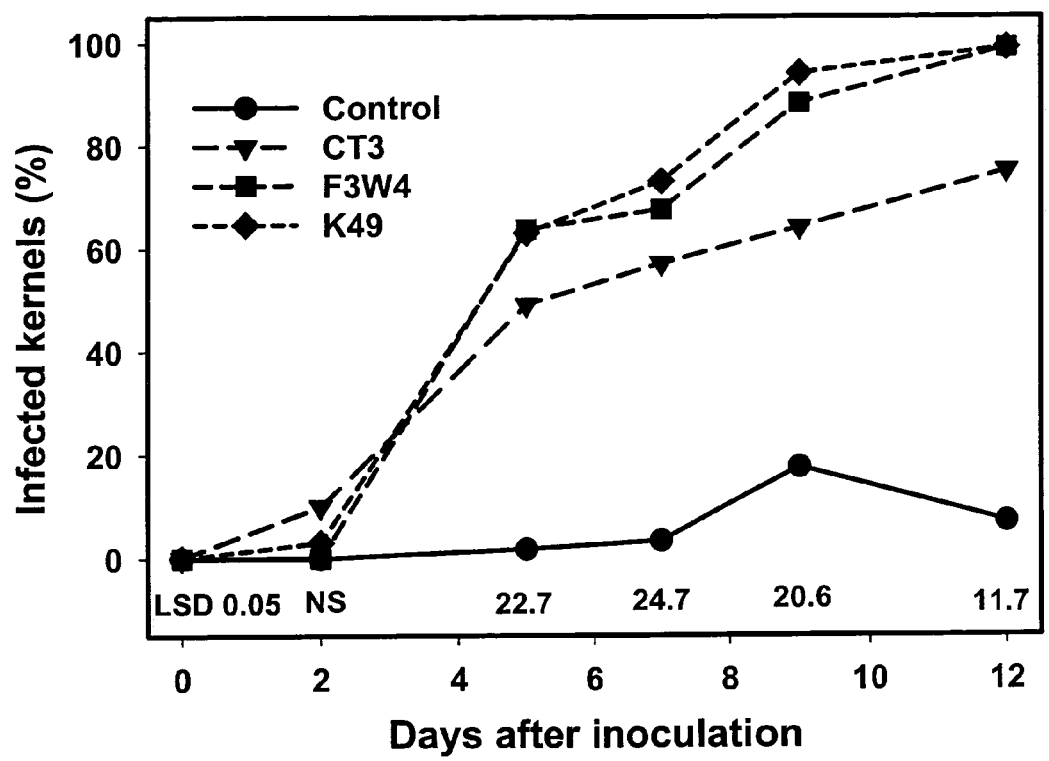
FIG. 1 depicts colonization of corn following pin point inoculation.

We have identified non-toxigenic and non-aflatoxigenic strains of *A. flavus* that show great promise for reduction of aflatoxin contamination in corn. We have evaluated the potential of *A. flavus* strains, the non-toxigenic strain K49 and the non-aflatoxigenic strain CT3, for reducing aflatoxin contamination in corn in the Mississippi Delta.

The addition of highly competitive, non-toxigenic strains of *A. flavus* to soil results in lower concentrations of toxins in agricultural crops. The non-toxigenic strains of *Aspergillus* become biocompetitive with the soil microflora and prevent the buildup of toxin-producing strains that normally occurs during late-season drought. Through biocompetition, the toxigenic strains of fungi found naturally in soil are replaced by non-toxigenic or non-aflatoxigenic strains added to the soil. Therefore, any crops subjected to late-season drought stress are invaded predominately by the biocompetitive strains which are unable to produce toxins.

The method of the invention is applicable to any agricultural commodity which is grown for human consumption and/or which is damaged by fungal toxins such as for example, peanuts, corn, cotton, and tree nuts.

For purposes of this invention, a fungal preparation or fungal agricultural biocontrol composition refers to a microbial preparation wherein the microbes comprise, consist essentially of, or consist of non-toxigenic or non-aflatoxigenic strains of *Aspergillus*. The fungal preparations may contain one or more of non-toxigenic strains or non-aflatoxigenic strains of *Aspergillus*. Non-toxigenic strains of *Aspergillus* include any strain which does not produce the toxins aflatoxin and cyclopiazonic acid (CPA). The agricultural biocontrol composition for purposes of this invention includes a non-toxigenic strain or strains of fungi on agriculturally acceptable carriers which may be any carrier which the fungi can be attached and are not harmful to the fungi or crops which are treated with the composition. An example of a non-toxigenic strain includes *A. flavus* K49. The fungi especially useful in the present invention are strains possessing the identifying characteristics of non-toxigenic *A. flavus* K49, designated NRRL 30797. These characteristics are the inability to produce the toxins aflatoxin and CPA and the ability to be biocompetitive when applied to soils growing agricultural commodities.

Non-aflatoxigenic strains of *Aspergillus* include any strain which does not produce the toxin aflatoxin, but which continues to produce cyclopiazonic acid (CPA). The agricultural biocontrol composition for purposes of this invention can include a non-aflatoxigenic strain or strains of fungi on agriculturally acceptable carriers which may be any carrier which the fungi can be attached and are not harmful to the fungi or crops which are treated with the composition. An example of a non-aflatoxigenic strain includes *A. flavus* CT3. The fungi which are also especially useful in the present invention are strains possessing the identifying characteristics of the non-aflatoxigenic *A. flavus* strain CT3, designated NRRL 30798. These characteristics are the inability to produce aflatoxin and the ability to be biocompetitive when applied to soils growing agricultural commodities.

Non-toxigenic and non-aflatoxigenic strains of *Aspergillus* are cultured as single strains on granular food sources, such as for example wheat, rice, rye, etc. These food sources contain approximately $10^6$ colony forming units (CFU) of fungi per gram of food source. For granular food sources such as wheat or rye, inoculated grains are incubated at about 35° C. After 24 h growth, the inoculated wheat was manually shaken and incubated for another 24 h and further homogenized by manual shaking. Colonization by the inoculant strain was confirmed by determining aflatoxin concentration in inoculants. The inoculated product is stored at about 5° C. until use.

The non-toxigenic and non-aflatoxigenic strains of *Aspergillus* are applied to soil in amounts effective to reduce toxin levels in agricultural commodities. As used herein "reduce toxin levels" refers to a reduction in amounts of toxin compared to that which would be expected in agricultural commodities which were not treated according to the methods of the present invention. Any accurate method of measuring and comparing toxin levels may be used for such comparisons, as would be apparent to those skilled in the art.

As used herein "in amounts effective", "an amount effective" or "an effective amount" refer to the amount of the fungal preparation administered wherein the effect of the administration acts to reduce toxin contamination of agricultural commodities. The granular or extruded products are applied to the soil at a rate of approximately 20 kilograms (kg) per hectare (ha). The soil surface around the plant provides a humid, protected environment which promotes growth and sporulation of the non-toxigenic and non-aflatoxigenic fungi. The strains can be applied as single strain compositions or the dried products can be mixed in about equal proportions to provide a composition made up of different strains of *Aspergillus*.

EXAMPLES

Having now generally described this invention, the same will be better understood by reference to certain specific examples, which are included herein only to further illustrate the invention and are not intended to limit the scope of the invention as defined by the claims.

Example 1

*Aspergillus flavus* Strains and Characterization Studies

*Aspergillus flavus* strains used in this study were isolated as described by Abbas et al. (2004, supra). These strains originated from single spores, and were maintained on Czapak agar slants and stored on silica gel (Horn, B. W., 2003, supra; Windels et al. 1988. *Phytopath.* 78: 107-109). Non-toxigenic *A. flavus* strain K49 (NRRL 30797) was isolated from corn grain from Sunflower County, Mississippi in 2001 (Abbas et al. 2005b. *Canad. J. Bot.*, in press). Non-aflatoxigenic *A. flavus* strain CT3 (NRRL 30798) was isolated in 2000 from Dundee silt loam soil, Washington County, Mississippi, in a field that had been continuously cropped in cotton for over ten years. The toxigenic *A. flavus* strain F3W4 (NRRL 30796) was isolated from Dundee silt loam soil in Sunflower County, Mississippi, in 2001 (corn/cotton rotation). These strains were selected based on their growth characteristics, sclerotia production and toxin profiles (Table 1). Aflatoxin production on potato dextrose agar (7 d) was determined using high performance liquid chromatography (HPLC) as described elsewhere (Abbas et al., 2004, supra). Cyclopiazonic acid was determined on yeast extract sucrose agar as described by Sobolev et al. (1998. *J. Assoc. Official Analytical Chem. Int'l.* 81: 57-60).

Production of both toxins was confirmed by liquid chromatography/mass spectroscopy (LC/MS) (Abbas et al., 2002, supra). Sclerotium production was determined according to Horn et al. (1996. *Mycologia* 88: 574-587). Briefly, isolates were grown on Czapek agar slants for 2 weeks at 30° C. in darkness. Sclerotium types S (<400 μm diameter) and L (>400 μm) were confirmed for each culture by measuring one hundred sclerotia as described by Abbas et al. (2005b, supra); sclerotium assessment was conducted at least three times for each strain. Radial growth rate was determined on dilute potato dextrose agar (Difco potato dextrose broth, 3 g/L in 18 g/L agar). Five replicate petri dishes (9 cm) were inoculated in the center with a 2-mm plug of a 3-d culture, incubated at 30° C., based on three measurements between 3 to 5 d.

A pin bar inoculation technique (King, S. B. & Scott, G. E. 1982. *Phytopath.* 72: 782-785; Windham et al. 2003. *J. Toxicol.-Toxin Rev.* 22: 313-325) was used to determine the relative colonization abilities of the three *A. flavus* strains on corn in the field in 2004. *Aspergillus* cultures were grown on PDA for 7 d. Conidia and mycelium were removed by scraping, then suspended in aqueous Tween 20 (0.2%), and adjusted to a concentration of about $5\times10^7$ conidia/ml. Corn ears (50 per treatment) were inoculated at mid-silking stage using a pin bar inoculator (100 mm-long row of 35-36 sewing needles mounted on wood or a plastic bar, each with 6 mm of the points exposed). Pin bars were dipped in spore suspensions, and the bars were pressed into the ear. At 2, 5, 7, 9 and 12 d after pin-bar inoculation, five inoculated ears were harvested per treatment, and the number of infected kernels and total number of kernels was determined based on visual assessment of sporulation. After assessing infected kernels, aflatoxin concentration in the infected kernels at 12 d after inoculation was determined by methanol extraction and HPLC according to Abbas et al. (2002, supra).

The characteristics of the *A. flavus* strains used in this study are summarized in Table 1. Based upon HPLC, ELISA and LC-MS confirmation of several repeated assays (>five assays on duplicate cultures), F3W4 produced high levels of aflatoxins B1 and B2, while F3W4 and CT3 produced cyclopiazonic acid. K49 produced neither aflatoxin B1 or B2 nor cyclopiazonic acid. Both the toxigenic strain F3W4 and the non-toxigenic isolate K49 produced abundant large sclerotia, whereas CT3 did not produce sclerotia, under our conditions. *Aspergillus flavus* sclerotia serve as a survival structures in soil and plant residues and upon germination will release conidia under appropriate conditions (Wicklow et al. 1982. *Mycologia* 74: 398-403; Wicklow et al. 1993. *Phytopathology* 78: 107-109). Small sclerotia type has been correlated with high aflatoxin production in *A. flavus* strains pathogenic to cotton while large sclerotial isolates produced less aflatoxin, with some isolates producing no aflatoxin at all (Cotty, P. J. 1989. *Phytopathology* 79: 808-814). On dilute PDA ($1/10^{th}$ strength), strain CT3 grew slower than either K49 or F3W4. Colonization of corn following pin point inoculation is presented in FIG. 1. The non-toxigenic strain K49 displayed a similar level of colonization of corn kernels as the toxigenic strain F3W4 while non-aflatoxigenic strain CT3 displayed significantly reduced colonization ($P<0.05$) at 9 and 12 d after inoculation. Total aflatoxin concentration in infected kernels from pin-bar inoculation with F3W4 was 34,184 compared to 6,998 ng/g in non-inoculated corn. However, aflatoxin concentration was only 190, and 4 ng/g in CT3 and K49 inoculated corn, respectively. The reduced levels of aflatoxin observed in K49 and CT3 pin-bar inoculated corn under field conditions is indicative of the capacity of the isolates to inhibit aflatoxin contamination by indigenous *Aspergilli*. Based upon growth rate, colonization of corn ears and sclerotium production, K49 is expected to have a greater degree of ecological competence compared to CT3.

TABLE 1

Characteristics of *Aspergillus flavus* strains used in this study.

| | *Aspergillus flavus* strains | | |
|---|---|---|---|
| Characteristics | CT3 | K49 | F3W4 |
| Sclerotia[a] | None | Large | Large |
| Aflatoxin B1[b] | ND[d] | ND | 32,000 to 47,500 |
| Aflatoxin B2 | ND | ND | 300 to 510 |

TABLE 1-continued Characteristics of *Aspergillus flavus* strains used in this study.

| | *Aspergillus flavus* strains | | |
|---|---|---|---|
| Characteristics | CT3 | K49 | F3W4 |
| Aflatoxin G1 | ND | ND | ND |
| Aflatoxin G2 | ND | ND | ND |
| Cyclopiazonic acid[b] | 800 to 1100 | ND | 3450 to 5100 |
| Radial growth rate[c] | 0.39 b | 0.54 a | 0.53 a |
| Pigmentation | Off-white | White | Yellow |

[a]Sclerotia production determined on Czapek agar, 14 d after incubation in continuous darkness; Large > 400 μm in diameter.
[b]Aflatoxin and cyclopiazonic acid concentrations in fungal biomass (ng/g, fresh weight) determined by HPLC; limits of detection = 4 ng/g; ranges based on 5 separate experiments.
[c]Radial growth rate (mm/d) determined on dilute (1/10$^{th}$ strength) potato dextrose agar, 3 to 5 d incubation in darkness at 37° C. Means of five replicates; means followed by the same letter do not differ significantly at the 95% confidence level.
[d]ND = none detected Example 2

Field Study: Inoculum Preparation

Wheat was used as the inoculant carrier. Wheat seed was soaked in water overnight, drained, placed in autoclavable bags (1 kg/bag with 200 ml water), and autoclaved for 55 min at 121° C. Starter cultures of *A. flavus* were grown on PDA in 9-cm Petri dishes at 30° C. for 5 d under continuous darkness. The autoclaved wheat was inoculated with the appropriate fungal culture (one 3 cm² portion of a 5 d PDA plate per bag) and incubated at 35° C. After 24 h growth, the inoculated wheat was manually shaken and incubated for another 24 h and further homogenized by manual shaking. Colonization by the inoculant strain was confirmed by determining aflatoxin concentration in inoculants.

Example 3

Field Study: Experimental design

Corn was planted 23 Mar. 2001, 6 Apr. 2002, 1 Apr. 2003, and 15 Apr. 2004 in a randomized complete block design with a split plot arrangement of treatments replicated four times. The treatments were application of: 1) non-infected autoclaved wheat seed; 2) *A. flavus* K49-treated wheat; 3) *A. flavus* CT3-treated wheat; 4) *A. flavus* F3W4-treated wheat; 5) mixture of *A. flavus* K49- and F3W4-treated wheat; and 6) mixture of *A. flavus* CT3- and F3W4-treated wheat. The six inoculation treatments were applied to the same experimental units over the four years of the study. Inoculations were made immediately after cultivation at growth stage V6 (Ritchie et al., 1997. Special Report No. 48, Iowa State University of Science and Technology, Cooperative Extension Service, Ames, Iowa), by scattering the treated wheat seed by hand in the middle furrows at rate of 20 kg/ha for each strain.

Individual plots consisted of eight rows that were 9.1 m long and spaced 102 cm apart. Inoculation treatments and subsequent data were collected from the four center rows of each plot. Plots were geo-referenced (GPS coordinates) to enable precise sampling and replanting.

The cultivars Pioneer 3225 (2001 and 2002) and Pioneer 32R25 (2003 and 2004) were planted at a rate of 75300 plants per ha. Soil tests were conducted by a commercial laboratory each year to determine N, P, and K fertility requirements for a yield goal of 12.5 mg/ha. A pre-plant application of the required P and K as super phosphate and muriate of potash was made along with 112 kg N/ha as urea. An additional application of 112 kg N/ha (urea: $NH_4NO_3$ solution) was made just prior to cultivation at growth stage V6. Weed control was achieved with the application of the herbicide acetochlor [2-chloro-N-(2-ethyl-6-methylphenyl)-N-(2 methoxy-1-methylethyl) acetamide] and atrazine [2-chloro-4-ethylamine-6-isopropylamine-5-triazine] in each year. In 2003 nicosulfuron [3-Pyridimeccarboxyamide, 2-[[(4,6-Dimethoxy-pyrimidin-2-yl) amino carbonyl]aminosulfonyl]-N—N-dimethyl was also applied for control of johnsongrass (*Sorghum halpense* (L.) pers.). Plots were furrow irrigated at growth stages R1 and R2 (approximately 25 mm of water each irrigation).

The effects of soil inoculation with toxigenic and non-toxigenic *A. flavus* strains on aflatoxin levels in corn grain are summarized in Table 2. In 2001 and 2002, there were high endemic levels of aflatoxin contamination in untreated corn (221 and 552 ng/g), respectively, while in 2003 and 2004 natural levels of aflatoxin were very low (8 ng/g). In both 2001 and 2002 there was a significantly lower aflatoxin concentration in corn kernels (P<0.05) from plots inoculated with CT3 or K49 compared to the untreated control or plots inoculated with toxigenic isolate F3W4. Inoculation with K49 significantly (P<0.05 level) decreased aflatoxin by 58 and 76% in 2001 and 2002, respectively, while inoculation with CT3 decreased aflatoxin concentration by 86 and 61% in 2001 and 2002 respectively, relative to non-inoculated controls. In 2001, aflatoxin levels in corn from plots inoculated with the toxigenic strain F3W4 were 167% greater than corn from uninoculated plots, while in 2002 aflatoxin levels in F3W4 and control treatments were similar. In both 2001 and 2002, aflatoxin levels in corn from plots inoculated with mixtures of inoculum were lower than those inoculated with the toxigenic isolate alone. In 2003 and 2004 when there were low levels of natural infection (8 ng/g), inoculation with F3W4 increased aflatoxin levels to 162 and 65 ng/g, respectively. Corn from plots inoculated with mixtures of either K49 or CT3 with F3W4 had significantly lower levels of aflatoxin compared to F3W4 alone (P<0.05). Aflatoxin levels in corn from plots inoculated with a mixture of strains K49 and F3W4 were typically lower than that in plots inoculated with a mixture of CT3 and F3W4 strains, indicating that K49 is perhaps a more aggressive competitor than CT3 (Table 2).

TABLE 2

Effect of soil treatment with toxigenic *Aspergillus flavus* F3W4, non-aflatoxigenic strains CT3 and K49, and mixtures of aflatoxigenic and non-aflatoxigenic strains on aflatoxin concentrations in corn.

| Treatment/ | Aflatoxin levels[a] (ppb) | | | |
|---|---|---|---|---|
| Isolate | 2001 | 2002 | 2003 | 2004 |
| Untreated | 221 b[b] | 552 a | 8 c | 8 c |
| F3W4 | 637 a | 610 a | 157 a | 65 a |
| CT3 | 32 e | 215 c | 8 c | 15 bc |
| K49 | 94 d | 131 b | 8 c | 10 c |
| CT3 + F3W4 | 251 b | 347 b | 58 b | 28 b |
| K49 + F3W4 | 167 c | 167 cd | 8 c | 17 bc |

[a]Mean aflatoxin concentration of four replicates in corn kernels determined by ELISA.
[b]Values followed by the same letter in a given column do not differ significantly at the 95% confidence level using Fisher's Least Significant Difference test.

There was no effect of prior inoculation in 2001 on *Aspergillus* propagule density in May 2002 (Table 3). However, inoculation with toxigenic strains, non-toxigenic strains or mixtures of *A. flavus* strains increased *A. flavus* soil propagule density in September of 2002 and both sampling times in 2003 (P<0.05). The lowest recovery of aflatoxigenic *A. flavus* isolates was found in soil inoculated with strains K49 and CT3.

TABLE 3

Effect of soil treatment with toxigenic and non-toxigenic *Aspergillus flavus* on soil propagule density of *Aspergillus* and recovery of aflatoxin-producing isolates from soil before inoculation and following corn harvest (2002 to 2004).

| Year/<br>Treatment | Propagule density *Aspergillus*<br>($\log_{10}$ colony forming units/g)[a] | | Toxigenic Isolates<br>(%)[b] | |
|---|---|---|---|---|
| | May 2002 | September 2002 | May 2002 | September 2002 |
| Untreated | 2.34 a[c] | 3.67 d | 56.3 b | 75 ab |
| F3W4 | 2.38 a | 3.90 bc | 81.3 a | 94 a |
| CT3 | 2.22 a | 3.83 c | 31.3 c | 0 c |
| K49 | 2.24 a | 3.83 c | 12.5 c | 6 c |
| CT3 + F3W4 | 2.34 a | 3.97 a | 68.8 ab | 69 ab |
| K49 + F3W4 | 2.28 a | 3.94 ab | 75.0 a | 50 b |
| Probability | NS[d] | 0.05 | 0.05 | 0.05 |

| | May 2003 | September 2003 | May 2003 | September 2003 |
|---|---|---|---|---|
| Untreated | 3.39 c | 3.26 b | 50.0 a | 56 b |
| F3W4 | 3.64 bc | 3.63 a | 82.5 a | 86 a |
| CT3 | 3.68 ab | 3.58 a | 15.0 b | 21 c |
| K49 | 3.67 ab | 3.62 a | 10.0 b | 16 c |
| CT3 + F3W4 | 3.79 a | 3.72 a | 70.0 a | 62 b |
| K49 + F3W4 | 3.64 ab | 3.55 a | 62.5 a | 63 ab |
| Probability | 0.05 | 0.05 | 0.05 | 0.05 |

| | May 2004 | September 2004 | May 2004 | September 2004 |
|---|---|---|---|---|
| Untreated | 2.77 c | 3.49 c | 49 b | 55.0 b |
| F3W4 | 3.28 b | 4.00 a | 85 a | 79.3 a |
| CT3 | 3.77 a | 3.94 ab | 17 c | 23.5 cd |
| K49 | 3.53 ab | 3.96 ab | 15 c | 9.3 d |
| CT3 + F3W4 | 3.68 a | 3.89 b | 47 b | 34.3 c |
| K49 + F3W4 | 3.81 a | 3.95 ab | 58 b | 37.5 c |
| Probability | 0.05 | 0.05 | 0.05 | 0.05 |

[a]$\log_{10}$ colony forming units *Aspergillus*/g soil. Mean of four replicates determined by serial dilution and plating on modified dichloronitroaniline rose bengal (MDRB) agar amended with 3% sodium chloride; colonies were counted after 5-d incubation.
[b]In 2002, 16 isolates (four per plot) and in 2003 and 2004, 120 isolates (30 per plot), were assayed for aflatoxin production based on fluorescence on β-cyclodextrin potato dextrose agar.
[c]Values followed by the same letter in a given column do not differ significantly at the 95% confidence level using Fisher's Least Significant Difference test.
[d]NS = not significantly different at the P < 0.05 level.

The distribution of toxigenic strains present in corn grain at harvest was determined in 2004 (Table 4). *A. flavus* was isolated from 100% of all kernels tested, regardless of treatment. The propagule density of *A. flavus* estimated in ground corn grain, however, was 10-fold higher in grain from inoculated plots compared to non-inoculated plots regardless of treatment. A similar frequency of toxigenic isolates was observed in whole kernels and ground grain samples. Greater than 90% of *A. flavus* isolates recovered from plots inoculated with F3W4 were toxigenic, while the lowest frequency of toxigenic isolates (<11%) was observed in K49 and CT3 inoculated plots. A similar frequency of toxigenic isolates was observed in corn from non-inoculated plots and plots inoculated with a mixture of CT3 and F3W4, while a lower frequency of toxigenic isolates was found in corn from plots inoculated with mixtures of K49 and F3W4. These results indicate that the non-aflatoxigenic isolates are colonizing the corn and actively competing against native strains or F3W4, and that K49 is perhaps a more effective competitor than CT3.

TABLE 4

Effect of soil treatment with toxigenic and non-aflatoxigenic *Aspergillus flavus* on recovery of toxigenic *A. flavus* from corn grain samples in 2004.

| Treatment | Whole kernel infected[a] (%) | Whole kernel toxigenic isolates[b] (%) | Ground grain colony forming units ($\log_{10}$/g)[c] | Ground grain toxigenic isolates[b] (%) |
|---|---|---|---|---|
| Untreated | 100 | 36.9 b | 3.39 b | 41.8 b |
| F3W4 | 100 | 93.6 a | 4.38 a | 91.7 a |
| CT3 | 100 | 0.0 d | 4.37 a | 10.8 de |
| K49 | 100 | 0.0 d | 4.39 a | 3.3 e |
| CT3 + F3W4 | 100 | 33.1 b | 4.37 a | 31.7 bc |
| K49 + F3W4 | 100 | 14.4 c | 4.37 a | 25.0 c |
| Probability | NS[e] | 0.05 | 0.05 | 0.05 |

[a]Forty surface sterilized corn kernels plated on modified dichloronitroaniline rose bengal (MDRB) agar amended with 3% sodium chloride; assessed for colonies of *Aspergillus* five d after plating.
[b]Isolates assessed for aflatoxin production based on fluorescence on β-cyclodextrin potato dextrose agar; 40 colonies per plot assessed from whole kernel isolates and thirty isolates per plot from ground corn.
[c]Colony forming units determined by serial dilution and plating on modified dichloronitroaniline rose bengal (MDRB) agar amended with 3% sodium chloride; colonies counted after five d incubation.
[d]Values followed by the same letter in a given column do not differ significantly at the 95% confidence level using Fisher's Least Significant Difference test.
[e]NS = not significantly different at the P < 0.05 level.

Example 4

Experimental Parameters

Aflatoxin concentration in corn was determined using a commercial ELISA kit (Neogen Corp., Lansing Mich.). Corn was hand harvested at maturity (20 top ears/plot) from center rows. The harvested corn was shelled, dried, and ground (20 mesh) using a Romer mill (Union, Mo.). Triplicate sub-samples (20 g) were extracted in 100 mL of methanol (70%) for 30 min on a high speed reciprocal shaker. The methanol extracts were filtered (Whatman # 1 filter paper), and the filtrate was analyzed by commercial ELISA kits (Neogen, Lansing, Mich.) according to Abbas et al. (2002, supra). The limit of detection in this assay is 5 ng/ha. In 2002 to 2004, *A. flavus* populations were enumerated from soils using modified dichloronitroaniline rose bengal (MDRB) agar according to Horn & Dorner (1998) amended with 3.0% sodium chloride (Griffin et al., 1975). Isolated colonies were plated on β-cyclodextrin (0.3%) PDA (CD-PDA) to assess aflatoxin production based on blue fluorescence of the colonies (Abbas et al., 2004, supra).

In 2004, whole corn grain and ground corn samples were assessed for *A. flavus* colonization and frequency of toxigenic isolates. Whole kernels were surface sterilized in 0.3% sodium hypochlorite solution for two minutes and seeds were rinsed three times in sterile distilled water. Forty kernels from each experimental plot were plated on MDRB agar and incubated for 5 d, and recovery of *A. flavus* colonies was recorded. Forty colonies per plot were transferred to CD-PDA and incubated for 5-d under continuous darkness at 30° C. for determining aflatoxin production. In addition, ground grain samples were homogenized in 0.2% water agar, serially diluted and plated on MDRB agar. Colony forming units were counted following 5 d incubation, and 30 colonies per plot were transferred to CD-PDA for assessment of aflatoxin production as described above.

Statistical Analysis: All field and laboratory data were analyzed using PROC GLM of the Statistical Analysis System (SAS, 2001).

Deposit of the Microorganisms: *Aspergillus flavus*, strain K49, designated NRRL 30797; *Aspergillus flavus*, strain CT3, designated NRRL 30798; and *Aspergillus flavus*, strain F3W4, designated NRRL 30796; have been deposited under the provisions of the Budapest Treaty on Dec. 10, 2004 with the U.S.D.A. Agricultural Research Service Patent Culture Collection (National Center for Agricultural Utilization Research, 1815N. University Street, Peoria, Ill., 61604).

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An isolated strain of *Aspergillus flavus*, strain K49 (NRRL 30797) or a variant thereof which is capable of inhibiting the growth of aflatoxin-producing fungi as well as their production of aflatoxin.

2. A biologically pure culture of *Aspergillus flavus* having all the identifying characteristics of strain NRRL 30797, wherein said identifying characteristics include the ability to inhibit the growth of aflatoxin-producing fungi and to inhibit aflatoxin production by native aflatoxin-producing strains of *Aspergillus* and hence reduce aflatoxin contamination of corn.

3. A non-toxigenic fungal biocontrol agent comprising the biologically pure *Aspergillus flavus* strain of claim 1 or 2 wherein said strain does not produce aflatoxin or cyclopiazonic acid and is capable of inhibiting both the growth of aflatoxin-producing fungi as well as the production of aflatoxin by native aflatoxin-producing strains of *Aspergillus* thus reducing aflatoxin contamination of corn.

4. A method for reducing aflatoxin contamination of corn comprising applying a biocontrol agent comprising the non-toxigenic strain of claim 1 or 2 in an amount effective to reduce subsequent aflatoxin contamination of said corn, wherein said non-toxigenic strain is applied to corn plants or to soil around corn plants and wherein said non-toxigenic strain competes with native *A. flavus* strains reducing growth of aflatoxin-producing fungi and subsequent biosynthesis of aflatoxin.

* * * * *